United States Patent [19]

Brandes et al.

[11] Patent Number: 4,914,119
[45] Date of Patent: Apr. 3, 1990

[54] FUNGICIDAL AGENTS

[75] Inventors: Wilhelm Brandes, Leichlingen; Helmut Kaspers, Leverkusen; Paul Reinecke, Leverkusen; Hans Scheinpflug, Leverkusen; Wolfgang Krämer, Wuppertal, all of Fed. Rep. of Germany

[73] Assignee: Bayer Aktiengesellschaft, Leverkusen, Fed. Rep. of Germany

[21] Appl. No.: 235,777

[22] Filed: Aug. 23, 1988

Related U.S. Application Data

[63] Continuation of Ser. No. 55,585, May 29, 1987, abandoned, which is a continuation of Ser. No. 526,934, Aug. 26, 1983, abandoned.

[30] Foreign Application Priority Data

Sep. 18, 1982 [DE] Fed. Rep. of Germany ....... 3234625

[51] Int. Cl.⁴ .......................................... A01N 43/64
[52] U.S. Cl. .................................................. 514/383
[58] Field of Search ........................................ 514/383

[56] References Cited

U.S. PATENT DOCUMENTS

| | | | |
|---|---|---|---|
| 3,912,752 | 10/1975 | Meiser et al. | 548/262 |
| 3,952,002 | 4/1976 | Kramer et al. | 548/262 |
| 4,251,512 | 2/1981 | Brandes et al. | 514/383 |

*Primary Examiner*—Douglas W. Robinson
*Assistant Examiner*—Joseph A. Lipovsky
*Attorney, Agent, or Firm*—Sprung Horn Kramer & Woods

[57] ABSTRACT

A synergistic fungicidal composition comprising a fungicidally effective amount of
(a) 1-(4-phenyl-phenoxy)-1-(1,2,4-triazol-1-yl)-3,3-dimethyl-butan-2-ol of the formula

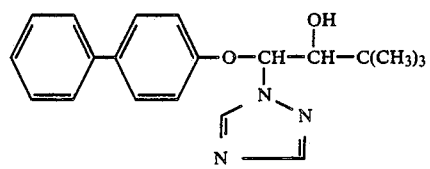

(b) plus another fungicidally active derivative of 1,2,4-triazole of the formula

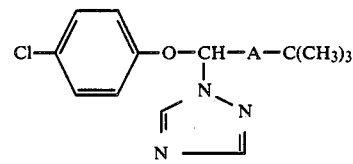

in which A is the keto group of the CH(OH) group.

9 Claims, No Drawings

FUNGICIDAL AGENTS

This application is a continuation of application Ser. No. 055,585, filed May 29, 1987, now abandoned which is a continuation of application Ser. No. 526,934, filed Aug. 26, 1983, now abandoned.

The present invention relates to new fungicidal synergistic active compound combinations of (a) the known compound 1-(4-phenyl-phenoxy)-1-(1,2,4-triazol-1-yl)-3,3-dimethyl-butan-2-ol and (b) other known fungicidally active derivatives of 1,2,4-triazole.

It is already generally known that mixtures containing 1,2,4-triazole derivatives, such as, for example, 1-(4-chloro-phenoxy)-3,3-dimethyl-1-(1,2,4-triazol-1-yl)-2-butanone, in combination with other known fungicides have a considerably higher action than the individual components (compare, for example, German Offenlegungsschrift (German Published Specification) 2,552,967. However, the activity of these active compound mixtures is not always completely satisfactory in all areas of use.

It has now been found that new specific active compound combinations of (a) 1-(4-phenyl-phenoxy)-1-(1,2,4-triazol-1-yl)-3,3-dimethyl-butan-2-ol of the formula

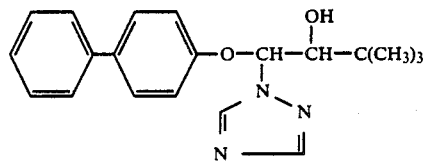

and (b) other fungicidally active derivatives of 1,2,4-triazole having the formula

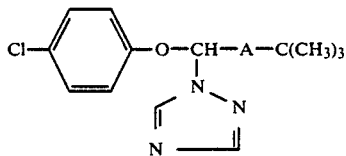

in which A represents the keto group or the CH(OH) group, have a particularly high fungicidal activity.

Surprisingly, the fungicidal action of the active compound combinations according to the invention is considerably higher than the action of the individual components and also than the sum of the individual components (synergistic effect). In particular, the expert could not predict that a mixture containing the active compound of the formula (I) and active compounds of the formula (II) having a very similar structure has a synergistic effect. The discovery of this specific combination represents a valuable enrichment of the art.

The above formulae (I) and (II) provide definitions of the active compounds to be used for the specific combinations according to the invention. These are the following compounds:

(I): short name BITERTANOL
(IIa): A=CO; short name TRIADIMEFON
(IIb): A=CH(OH); short name TRIADIMENOL The compounds mentioned are generally known (in this context, compare German Patent Specifications 2,201,063 and 2,324,010 and the corresponding U.S. Pat. Nos. 3,912,752 and 3,952,002).

Other active compounds can also be added (for example as a third component) to an active compound combination of the active compound of the formula (I) and the active compounds of the formula (II).

The weight ratios of the groups of active compounds in the active compound combinations can vary within relatively wide limits. In general, 0.001 to 50 parts by weight of active compound of the formula (II), preferably 0.01 to 20 parts by weight of the latter and particularly preferably 0.1 to 10 parts by weight, are present per part by weight of active compound of the formula (I).

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds in the concentrations required for combating plant diseases permits treatment of above-ground parts of plants, of vegetative propagation stock and seeds and of the soil.

The active compound combinations according to the invention have a very broad action spectrum and can be used against parasitic fungi which affect the above-ground parts of plants or attack the plants from the soil, as well as seed-borne causative organisms. Such active compound combinations have particularly practical imporatnce as seed dressing agents against phytophatogenic fungi which are transferred with the seed or occur in the soil and attack the crop plants from there. The diseases in question are damping off diseases, root rot and diseases of the stalk, stem, leaf, blossom, fruit and seed, which are caused, in particular, by species of Tilletia, Urocystis, Ustilago, Septoria, Typhula, Rhynchosporium, Helminthosporium and Fusarium. As a result of the systemic action of the partners in the mixture, the plants are frequently still protected, for a relatively long time after dressing, from causative organisms which can attack various parts of the shoot, for example powdery mildew fungi and rust fungi. In addition, the active compound combinations can also be used as soil treatment agents against phytopathogenic fungi, and they act against root rot and tracheomycoses, which are caused, for example, by causative organisms of the genera Pythium, Verticillium, Phialophora, Rhizoctonia, Fusarium and Thielaviopsis.

However, when applied directly to the above-ground parts of plants, the active compound combinations according to the invention also exhibit an outstanding action against causative organisms on various crop plants, such as powdery mildew fungi (species of Erysiphe, Uncinula, Sphaerotheca and Podosphaera, and *Leveillula taurica*), rust fungi, Venturia species, Cercospora species, Alternaria species, Botrytis species, Phytophthora species, Peronospora species, *Pyricularia oryzae* and *Pellicularia sasakii*.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gasesous at normal temperature and under normal pressure, for example aerosol propellants, such as halogenated hydrocarbons, as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, foaming, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001 percent by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The Use Examples which follow are for illustration.

EXAMPLE A

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

TABLE A

| Venturia test (apple)/protective | | |
|---|---|---|
| Active compound | Infestation in % at an active compound concentration of | |
| BITERTANOL (I) (known) | 0.0001% | 62 |
| TRIADIMEFON (IIa) (known) | 0.000012% | 72 |
| Mixture of (I) and (IIa) (mixing ratio 1:0.12) | 0.0001% +0.000012% | 30 |

EXAMPLE B

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

TABLE B

Drechslera graminea test (barley)/seed treatment
(syn. Helminthosporium gramineum)

| Active compound | Amount of active compound applied in mg/kg of seed | Diseased plants in % of the total plants emerged |
|---|---|---|
| No dressing | — | 28.8 |
| BITERTANOL (I) (known) | 500 | 11.1 |
| TRIADIMENOL (IIb) (known) | 200 | 12.3 |
| Mixture of (I) and (IIb) (mixing ratio 2.5:1) | 500 +200 | 0.0 |

It is understood that the specification and examples are illustrative but not limitative of the present invention and that other embodiments within the spirit and scope of the invention will suggest themselves to those skilled in the art.

We claim:

1. A fungicidal composition comprising a fungicidally effective amount of:
   (a) 1-(4-phenyl-phenoxy)-1-(1,2,4-triazol-1-yl)-3,3-dimethyl-butan-2-ol of the formula (I)

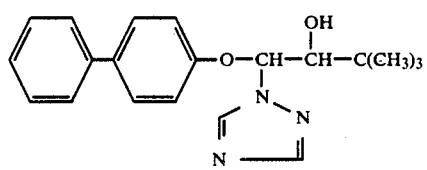

(b) plus another fungicidally active derivative of 1,2,4-triazole of the formula (II)

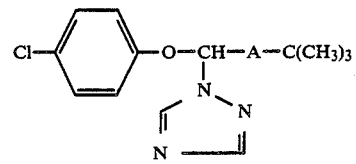

A is the keto group or the CH(OH) group and wherein the weight ratio of the compound of formula (I) to the compound of formula (II) is from 1:01 to 1:10.

2. A composition according to claim 1, in which (b) is the compound of the formula

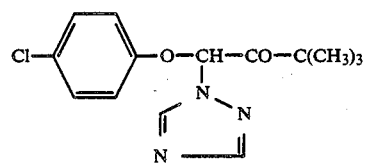

3. A process for combating fungi which comprise administering to such fungi or to a fungus habitat a fungicidally effective amount of a composition according to claim 2.

4. A composition according to claim 2 in which the weight ratio of the active compound of the formula (I) to the active compound of the formula (II) is about 8.3:1.

5. A composition according to claim 1, in which (b) is the compound of the formula

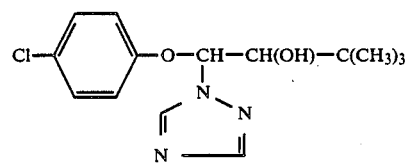

6. A process for combating fungi which comprise administering to such fungi or to a fungus habitat a fungicidally effective amount of a composition according to claim 5.

7. A composition according to claim 5, in which the weight ratio of the active compound of the formula (I) to the active compound of the formula (II) is about 2.5:1.

8. A composition according to claim 1, in which the active compound of the formula (I) is present in greater weight than the active compound of the formula (II).

9. A composition according to claim 1, in which the weight ratio of the active compound of the formula (I) to the active compound of the formula (II) is from about 2.5:1 to 8.33:1.

* * * * *